United States Patent [19]

MacLeod et al.

[11] Patent Number: 5,510,260

[45] Date of Patent: Apr. 23, 1996

[54] PROLACTIN SECRETING CELL LINE AND METHOD OF OBTAINING THE SAME

[75] Inventors: Robert M. MacLeod; Margaret V. MacQueen; Ivan S. Login, all of Charlottesville, Va.

[73] Assignee: Unversity of Virginia Patent Foundation, Charlottesville, Va.

[21] Appl. No.: 110,102

[22] Filed: Aug. 20, 1993

Related U.S. Application Data

[63] Continuation-in-part of Ser. No. 160,757, Feb. 26, 1988, abandoned.

[51] Int. Cl.$^6$ .................................................. C12N 5/06
[52] U.S. Cl. .................................................. 435/240.2
[58] Field of Search ........................... 435/70.1, 240.2, 435/240.21

[56] References Cited

U.S. PATENT DOCUMENTS 4,725,549   2/1988   Cooke et al. ................ 435/252.33

OTHER PUBLICATIONS

Judd, et al.; Endocrinology, vol. 123, No. 5, pp. 2341–2350; 1988.
Lamberts, et al.; Endocrinology, vol. 114, No. 6, pp. 2349–2353; 1984.

*Primary Examiner*—George C. Elliott
*Attorney, Agent, or Firm*—Sheldon H. Parker

[57] ABSTRACT

A unique clonal cell line, designated MMQ, is disclosed. The MMQ cell line is characterized by the presence of functional dopamine receptors and the secretion of only the prolactin hormone. The MMQ cell line is derived from the pituitary tumor 7315a, the tumor being characterized by the secretion of both prolactin and adrenocorticotrophin and an absence of functional dopamine receptors. The cell line also contains functional somatostatin and vasoactive intestinal polypeptide receptors. The cell line is prepared by dispersing the 7315a pituitary tumor cells into a population of single cells and incubating the cells for a period of time in plastic flasks containing incubation medium. Two distinct populations of cells are formed, one adhering to the plastic flask and the other floating within the plastic flasks. The floating cells are removed and cloned.

5 Claims, No Drawings

PROLACTIN SECRETING CELL LINE AND METHOD OF OBTAINING THE SAME

The present invention was made with the assistance of the U.S. Government funding (NIH Grant CA07353 and CA38228). The U.S. Government may have some rights in the invention.

CROSS-REFERENCE TO RELATED APPLICATION

This is a continuation-in-part of application Ser. No. 07/160,751 filed on Feb. 26, 1988 abandoned.

This application is a C-I-P of co-pending application, Ser. No. 07/160,757, filed Feb. 26, 1988, the subject matter of which is incorporated by reference as though cited in full.

BACKGROUND OF THE INVENTION

1. Field of the Invention

The invention relates to the medical arts, and, in particular, to the art of obtaining a cloned cell line expressing functional dopamine receptors and secreting only a single hormone. While many cloning methods have become standard and well known, the instant invention, in addition to including a unique cell line, includes a unique methodology for obtaining the cell line.

2. Brief Description of the Prior Art

Prolactin, also known as luteotropic hormone (LTH) or luteotropin, is a protein hormone produced by the pituitary gland of mammals and acts with other hormones to initiate secretion of milk by mammary glands. The hormone has other functions which are known, but many functions remain unknown. For instance, the function of prolactin in males is not generally understood. It is known that, in humans, prolactin is somewhat similar to human growth hormone.

Adrenocorticotropic hormone (ACTH), also known as corticotropin, is a polypeptide hormone formed in the pituitary gland. ACTH is known to regulate the activity of the outer region (cortex) of the adrenal glands. In mammals, the action of ACTH is limited to the areas of the adrenal cortex in which the glucocorticoid hormones are formed. It is further known that the secretion of ACTH by the pituitary is itself regulated by another polypeptide that is discharged from the hypothalamus in response to impulses transmitted by the nervous system.

Dopamine, also known as hydroxytyramine, is a nitrogen-containing, organic compound formed during the metabolism of the amino acid tyrosine. Dopamine functions as a neurotransmitter. The effects of the deficiency of dopamine is manifest in the form of Parkinson's disease.

Dopamine inhibits prolactin-release from normal anterior pituitary cells. However, the pituitary cell population is heterogeneous, and presently established prolactin-secreting cell lines, as subsequently described, do not express functional dopamine receptors, thereby making the study of control mechanisms difficult.

This problem has persisted in that, until now, all pituitary cell lines have secreted multiple types of hormones, none of which have functional dopamine receptors, thereby rendering the study of hormone secretion difficult.

SUMMARY OF THE INVENTION

An object of the instant invention is to provide a clonal cell line characterized by the secretion of the hormone prolactin and no other pituitary hormones, and by the presence of a functional dopamine receptor. The cell line has been designated MMQ.

Preferably, the MMQ cell line is derived from a pituitary tumor 7315a which secretes both prolactin and adrenocorticotrophin. The pituitary tumor 7315a as a whole contains dopamine receptors which have little biological function.

The dopamine receptors are negatively coupled to adenylate cyclase by a GTP-binding protein.

The cell line comprises dispersing pituitary tumor cells into a population of single cells by incubation for a period of time in plastic flasks containing incubation medium. The two distinct populations of cells are separated by adhesion, with one population adhering to the plastic flask and the other population floating in the medium. The population of floating cells is removed and cloned to produce a clonal cell line characterized by the secretion of prolactin hormone and no other pituitary hormones, and by the presence of functional dopamine receptors.

Preferably, the dispersing step comprises incubating tumor pieces with collagenase in tissue culture flasks containing RPMI-1640 as the incubation medium.

The cloning step preferably includes diluting the floating cells with incubation medium and culturing an amount of diluted cells in culture plates by feeding culture medium over a period of time.

Known cloning techniques may be employed after the floating cells are obtained. The most salient feature of the aforementioned method is the use of adhesion to a plastic flask to separate one population of cells from another. A surprising discovery was made in that the floating cells constitute a pure prolactin-secreting cell line with functioning dopamine receptors.

RPMI-1640 is a known incubation medium and is well known to those skilled in the art.

By way of further background, it is noted that in Cell Culture Labfax, Edited by Butler et al, BIOS Scientific Publishers Limited, Academic Press, (1992) United Kingdom, at pages 82 and 83, the basic method of cloning cells is disclosed. The disclosure is incorporated herein by reference, as though cited in full. Butler et al indicate that in cell culture the term cloning means the production of a cell culture in which all of the cells are derived from a single cell. Thus the cells are all genetically identical. The term cloning is employed herein consistent with Butler et al.

DETAILED DESCRIPTION OF THE INVENTION

The instant invention solves the aforementioned problem by providing a cell line that is composed of only a a single cell type that contain functional dopamine receptors and secretes only prolactin and no other known pituitary hormone. The cell line has been designated MMQ.

The MMQ cell line was derived from the pituitary tumor 7315a, a cell line that secretes both prolactin and adrenocorticotrophin (ACTH). The MMQ cell line was obtained by cutting a 7315a tumor into small pieces and then dispersing the pieces into a population of single cells by means of incubating tumor pieces with collagenase. These cells were incubated in tissue culture flasks containing RPMI1640, 5% NHS, 5% FCS. After 48 hours of incubation, the cells were observed to be composed of two distinct populations. One population consisted of those cells that adhered to the plastic flasks and the other population consisted of those cells that did not adhere and instead floated in the incubation medium.

The floater cells, which we have designated MMQ, were small granular and irregularly shaped in contrast to the cells that adhered to the flasks. The MMQ cells took up large amount of $^{45}Ca^{2+}$ and had a modest response to maitotoxin. The addition of dopamine blocked the maitotoxin-induced efflux of $^{45}Ca^{2+}$.

On a later date and based on these results another 7315a tumor was dispersed with collagenase as described above. Two plastic culture flasks were each seeded with $16.8 \times 10^6$ cells and were incubated for 48 hours in 95% air-5% $CO_2$. The incubation medium containing the non-adherent cells was decanted and pooled and contained $6.8 \times 10^6$/ml cells. These are the cells that floated in the incubation medium and did not adhere to the plastic walls of the flask. This cell suspension was diluted with RPMI-1640 so that the final suspension contained 28.3 cells/ml. In this manner, each well in four 24 well plates were seeded with 100 µl of this suspension (2.8 cells)/well and had 0.9 ml of incubation medium added that contained antibiotics and serum and cultured in 5% $CO_2$-95% air at 37° C.

It is noted by Butler et al, in Cell Culture Labfax, that in practice, cells are seeded into wells at very low densities. The procedure employed herein is consistent with the Butler et al publication. After about 3 weeks, some wells had small clumps of cells whereas others appeared empty or had a few scattered cells. All wells were fed with 0.5 ml RPMI. After about two weeks, clumps of cells from 20 wells were transferred in a sterile manner to new wells containing RPMI. About two weeks later, all wells were fed with RPMI. About four weeks later, clumps of cells were transferred to new wells and re-fed and then re-fed again three weeks later. About two weeks later, the contents of each of the 20 wells was split into two groups and plated into wells. About nine days later, the cells were re-fed with RPMI. One week later, the contents of each well was split and re-fed. The same was done one week later. Ten days later, the contents of these wells was transferred to 12 well plates and cultured. About one week later, the contents of the wells was split and cells were transferred to new 12 well plates. A week later, all wells were re-fed with fresh RPMI. About two weeks later, cells were split and transferred to new plates and RPMI. Eleven days later, all cells in wells were transferred to small 25 cm$^3$ flasks containing 15 ml RPMI. About two weeks later, all cells were transferred to large 75 cm$^3$ flasks with 30 ml RPMI. Five days later, enough cells had been generated to allow for the cold storage of cells after centrifugation. Accordingly, the cells were frozen in a solution of 7% DMSO in RPMI. The contents of one flask were not frozen but rather the cells therein were continued to be cultured in RPMI. At approximately one week intervals thereafter, the cell cultures were split and grown in fresh RPMI incubation medium until two and one half months later, when the cell characteristics were first analyzed as described herein. The homogenates of the cells were tested for ACTH. Experiments showed that ACTH was not present in the cell homogenates or cell culture medium. Moreover, immunocytochemistry examination also concluded that the cells contained no ACTH.

The prolactin and ACTH-secreting 7315a tumor has dopamine receptors but they are not functional. MMQ, a homogeneous prolactin-secreting cell line possessing functional dopamine receptors was isolated from this tumor. This isolation involved the use of the solid tumor which was dispersed with collagenase and cultured in RPMI-1640 containing normal horse and calf serum. As previously mentioned, one population is adherent to plastic-ware and the other is non-adherent. The non-adherent cell has been designated MMQ.

In the non-adherent cells, but not in the adherent ones, dopamine inhibits prolactin release that was stimulated by maitotoxin. Maitotoxin is known as a calcium channel activator.

The clonal cell line MMQ, was derived from the non-adherent cells which secrete only prolactin and no detectable amounts of ACTH or any other pituitary hormones. As previously mentioned, dopamine inhibits (50–80%) maitotoxin-induced prolactin release from these cells.

Further studies included measurement of the cAMP levels in the MMQ cells. Vasoactive intestinal peptide (VIP), forskolin, and choleratoxin each increased cellular cAMP levels, and dopamine (50–1000 nM) inhibited each response in a concentration-dependent manner as it does in normal pituitary cells. Haloperidol, which is a dopamine receptor antagonist, blocked the dopaminergic effects, as did pre-treatment of the cells with pertussis toxin, which is an inactivator of a receptor-associated GTP-binding protein. Somatostatin (SRIF 100 nM) also significantly attenuated (30%) forskolin and VIP-stimulated cAMP generation, but to a lesser extent than the attenuation caused by 1 µM of dopamine (50%).

MMQ cells grow rapidly (dividing time less than 24 hours), and after more than a year in culture, the effect of dopamine on prolactin-release has not been altered.

The MMQ cell line secretes only prolactin and contains dopamine receptors that are negatively coupled to adenylate cyclase by a GTP-binding protein. These cells also possess functional SRIF and VIP receptors. The homogeneous cell line, MMQ, provides a valuable tool for determining the mechanisms through which dopamine, VIP and SRIF regulate cellular function.

By way of contrast, Reymond et al, Acta Endocrinolgica 1984, 106:459–470, discloses a clonal strain of rat pituitary tumor cells which were isolated from tumor 7315a and designated 235-1 cells. These cells, which were derived from the adherent cells (as contrasted with the floaters of the instant invention), were noted (at page 459) to secrete prolactin as well as trace quantities of GH and to be unaffected by dopaminergic agonists and antagonists. Specifically, the article indicates that "After 3–4 weeks in culture, cells growing from the explants as a monolayer were dislodged from the flasks using Ca- and Mg-free Hanks' balanced salt solution containing 0.5% trypsin and 0.02% EDTA." The standard procedure of infinite dilution to obtain a clone line, as disclosed by Reymond et al corresponds to the procedure of the instant invention. Cronin et al, Molecular and Cellular Endocrinology, 28(1982) 229–246, Elsevier Scientific Publishers Ireland, Ltd., discloses that the 235-1 clone derived from the 7315a transplantable tumor was characterized by secreting rat prolactin. In radioligand binding studies using the dopamine antagonist [$^3$H]spiperone, no evidence of a dopamine receptor was obtained. It is further noted that in addition, the induction of a prolactin-secreting solid tumor in rats by subcutaneous innoculaton of the 235-1 cells failed to induce measurable dopamine receptors associated with rat tumor cells. It was concluded that the 235-1 clone does not express dopamine receptors and that the presence of dopamine receptors is obligatory for the typical inhibitory effects of bromocriptine on prolactin release and pituitary cell growth. The critical distinction between a clone line derived from adherent cells and a clone line derived from non-adherent cells (floaters) is evident from a comparison of the results obtained in accordance with the instant invention and the results obtained by Reymond et al.

The MMQ cell line was deposited with the American Type Culture Collection, 12301 Parklawn Drive, Rockville, Ma. 20852, on Nov. 16, 1990. The line has been assigned number CRL 10609 PATENT and deposited on behalf of the University of Virginia Patents Foundation. The depositor is Dr. Robert M. MacLeod, University of Virginia Health Science Center, Department of Medicine, Charlottesville Va. 22809.

What is claimed is:

1. The clonal cell line MMQ, said MMQ cell line being on deposit and identified in the American Type Culture Collection as CRL 10609 and characterized by the presence of dopamine receptors and the secretion of only the prolactin hormone.

2. The cell line of claim 1 wherein said MMQ cell line is derived from the pituitary tumor 7315a, said pituitary tumor being characterized by secreting both prolactin and adrenocorticotrophin and having an absence of functional dopamine receptors.

3. The clonal cell line of claim 1 wherein the functional dopamine receptors are capable of being negatively coupled to adenylate cyclase by a GTP-binding protein.

4. The cell line of claim 1 further comprising functional somatostatin receptors.

5. The cell line of claim 1 further comprising functional vasoactive intestinal polypeptide receptors.

* * * * *